(12) United States Patent
Clark et al.

(10) Patent No.: US 9,044,156 B2
(45) Date of Patent: Jun. 2, 2015

(54) CATHETER WITH IMPROVED SAFETY LINE FOR DISTAL TIP AND RELATED METHOD

(71) Applicant: Biosense Webster (Israel) Ltd., Yokneam (IL)

(72) Inventors: Jeffrey Clark, Castaic, CA (US); Maria Duarte, Chino, CA (US); Erica Lovejoy, La Puente, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 13/730,745

(22) Filed: Dec. 28, 2012

(65) Prior Publication Data

US 2014/0187893 A1      Jul. 3, 2014

(51) Int. Cl.
*A61B 5/042* (2006.01)
*A61B 18/14* (2006.01)
*A61B 18/00* (2006.01)

(52) U.S. Cl.
CPC ............. *A61B 5/042* (2013.01); *A61B 18/1492* (2013.01); *Y10T 29/49117* (2015.01); *A61B 2018/00029* (2013.01)

(58) Field of Classification Search
CPC .. A61B 5/042; A61B 5/0422; A61B 18/1492; A61N 1/056
USPC .............................. 600/374; 606/41; 607/122
See application file for complete search history.

(56) References Cited

U.S. PATENT DOCUMENTS

| | | | |
|---|---|---|---|
| 5,372,587 A | 12/1994 | Hammerslag et al. | |
| 5,782,900 A | 7/1998 | de la Rama et al. | |
| 5,836,875 A * | 11/1998 | Webster, Jr. | 600/374 |
| 5,964,757 A | 10/1999 | Ponzi | |
| 6,006,123 A | 12/1999 | Nguyen et al. | |
| 6,134,463 A * | 10/2000 | Wittkampf et al. | 600/374 |
| 6,171,275 B1 * | 1/2001 | Webster, Jr. | 600/374 |
| 6,477,396 B1 * | 11/2002 | Mest et al. | 600/374 |
| 6,733,499 B2 * | 5/2004 | Scheib | 606/41 |
| 7,018,303 B2 | 3/2006 | Yamamoto | |
| 7,163,537 B2 * | 1/2007 | Lee et al. | 606/41 |
| 7,731,693 B2 | 6/2010 | Melsheimer | |
| 2007/0156133 A1 * | 7/2007 | McDaniel et al. | 606/41 |
| 2008/0255540 A1 | 10/2008 | Selkee | |
| 2008/0281320 A1 * | 11/2008 | Scheib | 606/41 |

(Continued)

FOREIGN PATENT DOCUMENTS

EP       2 382 935 A1    4/2011

OTHER PUBLICATIONS

Extended European Search Report for Application No. 13199546.6-1652 dated May 14, 2014, 4 pgs.

*Primary Examiner* — Lee S Cohen

(74) *Attorney, Agent, or Firm* — Christie, Parker & Hale, LLP

(57) ABSTRACT

A catheter includes a tip electrode with a shell and a support member to provide a plenum chamber. The support member is formed with a U-shaped passage for a safety line to wrap around and secure the support member (with the shell affixed thereto) to the catheter. Additional passages are formed in the support member to accommodate components such as irrigation tubing, lead wire and thermocouple wire pair. A method of manufacture provides distal installation and/or anchoring of the safety line, lead wire and thermocouple wire pair in the support member prior to sealing the support member and mounting the shell.

21 Claims, 14 Drawing Sheets

(56) References Cited

U.S. PATENT DOCUMENTS

2009/0312756 A1* 12/2009 Schlesinger et al. ............ 606/41
2010/0057072 A1 3/2010 Roman et al.
2010/0168827 A1 7/2010 Schultz
2011/0152857 A1 6/2011 Ingle
2012/0035466 A1 2/2012 Tegg
2012/0157991 A1* 6/2012 Christian ....................... 606/41

* cited by examiner

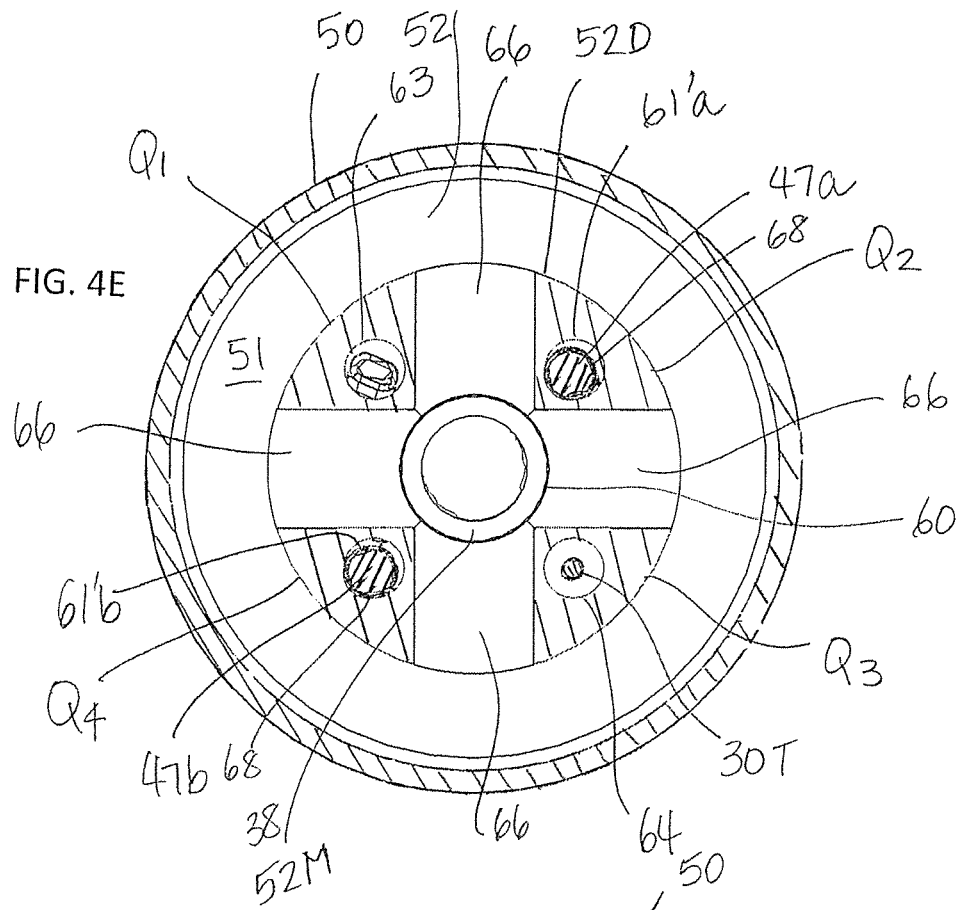
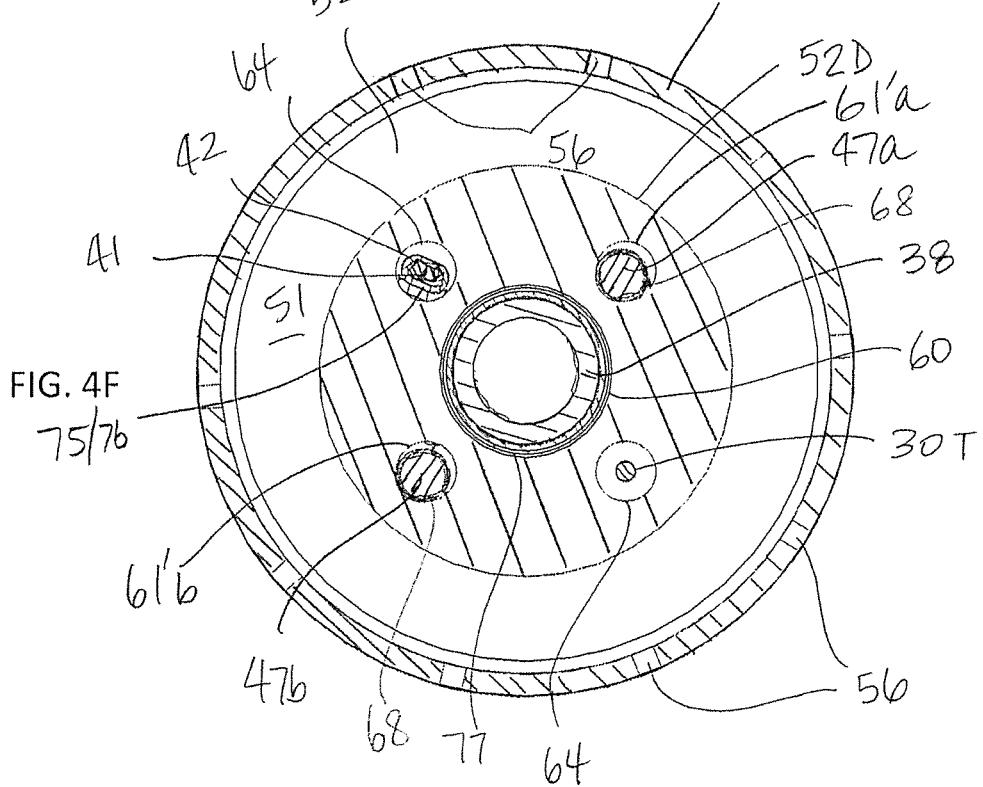

CATHETER WITH IMPROVED SAFETY LINE FOR DISTAL TIP AND RELATED METHOD

FIELD OF INVENTION

The present invention relates to catheters that have an active distal portion, including a tip electrode, particularly useful for ablation and sensing electrical activity of heart tissue.

BACKGROUND OF INVENTION

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical procedure involves the insertion of a catheter having a tip electrode at its distal end into a heart chamber.

A typical mapping or ablation catheter has an elongated catheter body comprising a flexible lumened tubing, a more distal section comprising another flexible lumened tubing, and a tip electrode at distal end of the second tubing. Bonding adhesive is applied to affix the tip electrode to the second tubing. As a tissue contact area of the catheter, the tip electrode is subjected to a variety of stresses and strains during mapping and ablation. Repeated exposure to axial and lateral loads can weaken the bond between the tip electrode and the catheter. As the distal-most component of a catheter and hence the last component of the catheter to exit the patient's body, extra care and attention is given to its attachment to the catheter as detachment of the tip electrode would be a significant safety breach for the patient. Many catheter designs make use of a primary adhesive bond supplemented by additional structural joints in the form of a puller wire attachment directly to the tip electrode. The tip electrode may also be tethered by a lead wire or thermocouple wires. However, design failure mode effects analysis (DFMEA) requires redundant safety structures to reduce the risk of detachment.

Conventional catheters may provide a safety line that is tied or attached to the tip electrode. Typically an eyelet or loop of stainless steel or the like is soldered to a distal end or stem of the tip electrode and a distal end of the safety line is fed through the eyelet and knotted. However, eyelets are expensive and very time-consuming to manufacture. Moreover, crimping, tie offs, and tight bends in the safety line around the eyelet and within the knot induce stress concentrations causing premature wear and tear which can significantly reduce the tensile load carrying capability of the safety line. Additionally, the eyelet-knot arrangement occupies precious space in the tight quarters of a distal tip.

Accordingly, it is desirable that a catheter provide a tip configuration that can better accommodate a safety line and reduce the stress and strain so the safety line can more fully utilize its tensile load carrying capability. It is also desirable that the tip configuration make more efficient use of the space in the distal tip while accommodating the safety line without interfering with the housing and function of other components of the distal tip.

SUMMARY OF THE INVENTION

The present invention is directed to a catheter having a tip configuration that mitigates stress concentrations found in safety line attachments to a catheter tip electrode. The tip configuration advantageously provides a U-shaped passage or conduit having an inlet, a U-turn and an outlet through which a flexible safety line is threaded. Two proximal portions of the safety line exit from the U-shaped passage and pass through the catheter and enter a control handle where the ends of the safety lines are anchored. The looping of the safety line around the U-shaped passage generally behaves as a rope over a pulley where the effective lifting strength at the pulley is twice that of the tension on the rope. Accordingly, the effective load-carrying capacity of the safety line in securing the tip electrode is about twice that of the tensile strength of an individual safety line.

In one embodiment of the present invention, the catheter has an elongated catheter body, a tip electrode distal to the catheter body and a safety tensile member or safety line. The tip electrode has a support member having a passage portion defining a rounded distal surface, and a shell mounted on the support member, wherein the safety line has a line portion positioned in the passage portion to pass around the rounded distal surface. Securing the tip electrode, the safety line has two ends, at least one of which is anchored to the catheter, for example, a control handle proximal of the catheter body. The passage portion is U-shaped, such that the safety line has two proximal portions extending proximally from the support member to pass in parallel through the catheter body.

In a detailed embodiment, the shell and the support member define a cavity and the support member has at least one additional passage providing fluid communication between the catheter body and the cavity. The shell has at least one fluid port configured to allow fluid communication between the cavity and outside the shell. The support member has at least one additional passage configured to receive at least one component passing between the catheter body and the tip electrode. The at least one component may include a lead wire, a thermocouple wire, an irrigation tubing and/or a position sensor cable.

In a detailed embodiment, the at least one component has an enlarged distal end and the at least one additional passage has a wider distal portion to receive and anchor the enlarged distal end. This arrangement allows the components to be installed distally into the tip electrode and the components to be efficiently housed and arranged in the space-confined distal tip region without interfering with each other.

The present invention also includes a method of manufacturing a catheter tip electrode comprising providing a tip electrode support member and a shell, forming in the support member a passage defining a rounded distal surface, extending a safety tensile member in the passage to pass around the rounded distal surface, the safety tensile member having two portions extending proximally of the rounded distal surface, and mounting the shell on the support member.

The method may include providing an exposed rounded distal surface and sealing the rounded distal surface prior to mounting the shell on the support member. The method may also include forming in the support member at least one additional passage configured to receive an irrigation tubing, a lead wire, a thermocouple wire and/or a position sensor cable.

The method may further include providing an enlarged distal portion in the at least additional passage, and providing an enlarged distal end in the component for anchoring in the enlarged distal portion of the at least additional passage.

BRIEF DESCRIPTION OF THE DRAWINGS

These and other features and advantages of the present invention will be better understood by reference to the following detailed description when considered in conjunction with the accompanying drawings wherein:

FIG. 4E is an end cross-sectional view of the tip electrode of FIG. 4, taken along line E-E.

FIG. 4F is an end cross-sectional view of the tip electrode of FIG. 4, taken along line F-F.

FIG. 4I is an end-cross-sectional view of the tip electrode of FIG. 4, taken along line I-I.

DETAILED DESCRIPTION OF THE INVENTION

Figure 1:
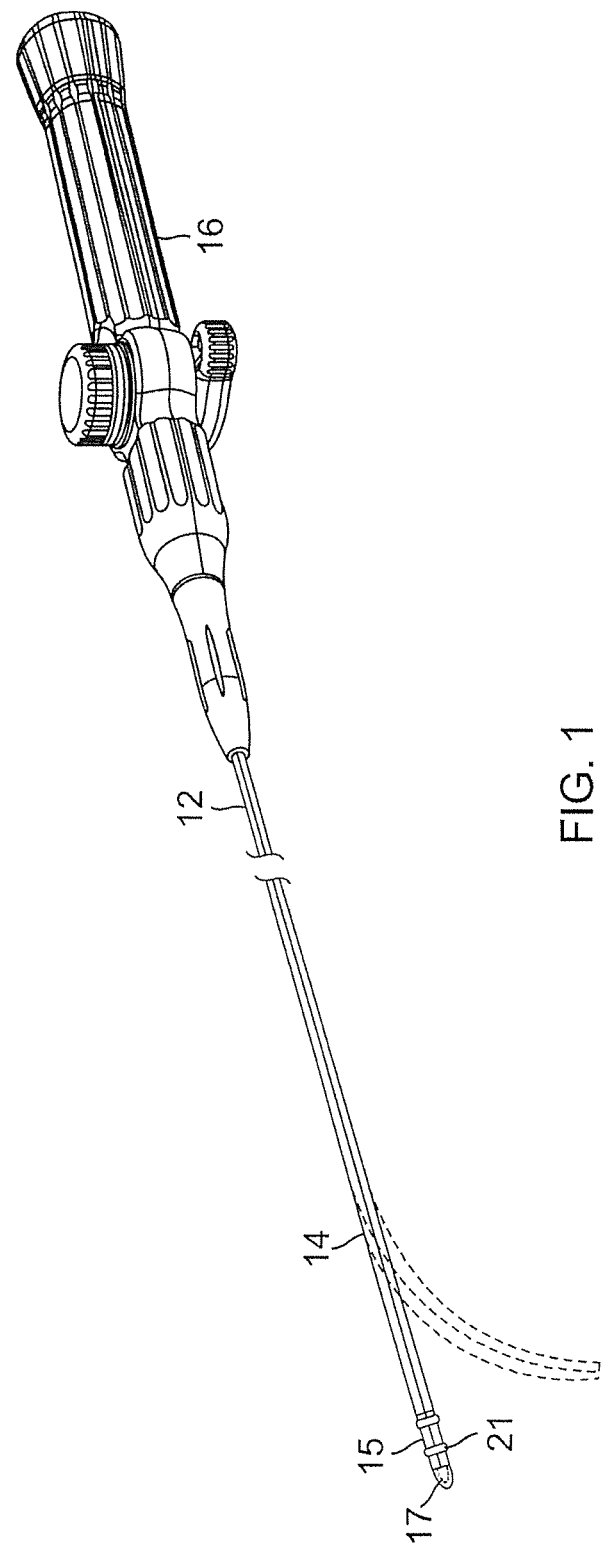
FIG. 1 is a perspective view of a catheter in accordance with an embodiment of the present invention.

FIG. 1 illustrates an embodiment of a catheter 10 with an improved distal tip configuration to accommodate a safety tensile member or line that secures a tip electrode with reduced stress and strain on the safety line. In accordance with a feature of the present invention, the safety line is threaded through or looped around a member of the tip electrode to secure the tip electrode. The catheter 10 has an elongated catheter body 12 with proximal and distal ends, an intermediate deflectable section 14 at the distal end of the catheter body 12, and a distal section 15 with a tip electrode 17 adapted for mapping and/or ablation with irrigation. The catheter also includes a control handle 16 at the proximal end of the catheter body 12 for controlling deflection (single or bi-directional) of the intermediate section 14 relative to the catheter body 12.

Figure 2A:
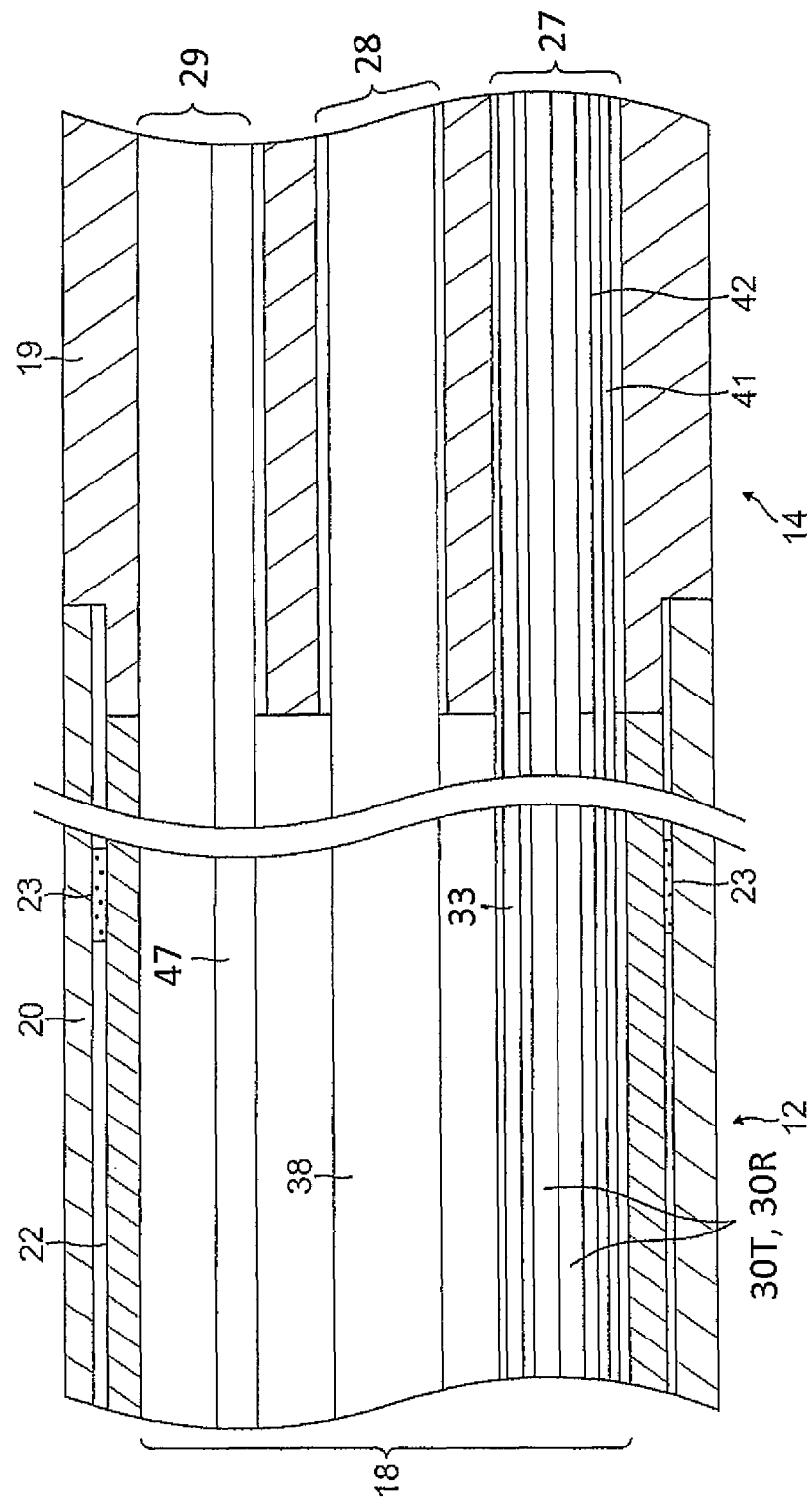
FIG. 2A is a side cross-sectional view of the catheter of FIG. 1, including a junction between a catheter body and a deflectable intermediate section, taken along a first diameter.
Figure 2B:
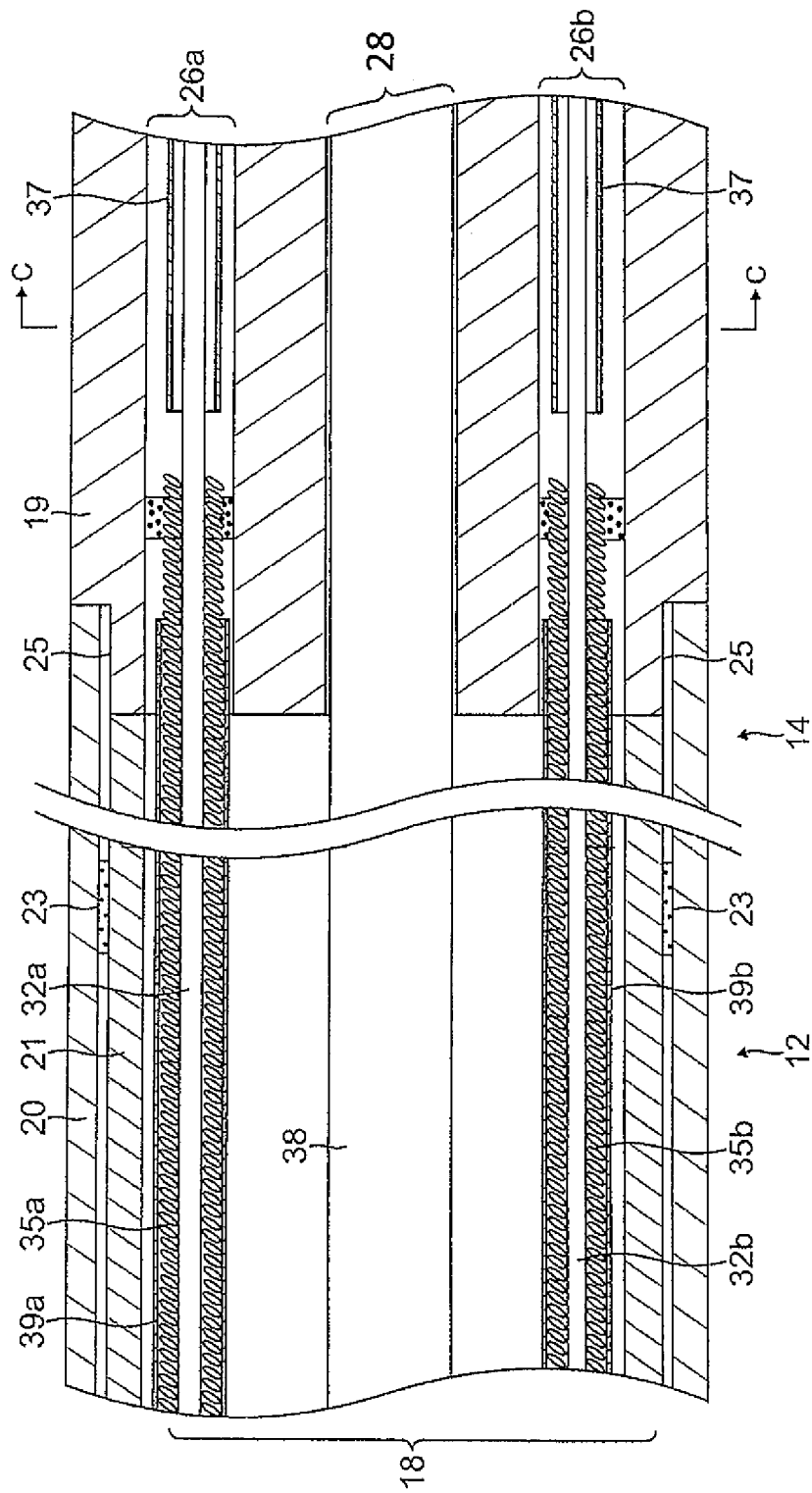
FIG. 2B is a side cross-sectional view of the catheter of FIG. 1, including a junction between a catheter body and a deflectable intermediate section, taken along a second diameter generally orthogonal to the first diameter of FIG. 2A.
Figure 2C:
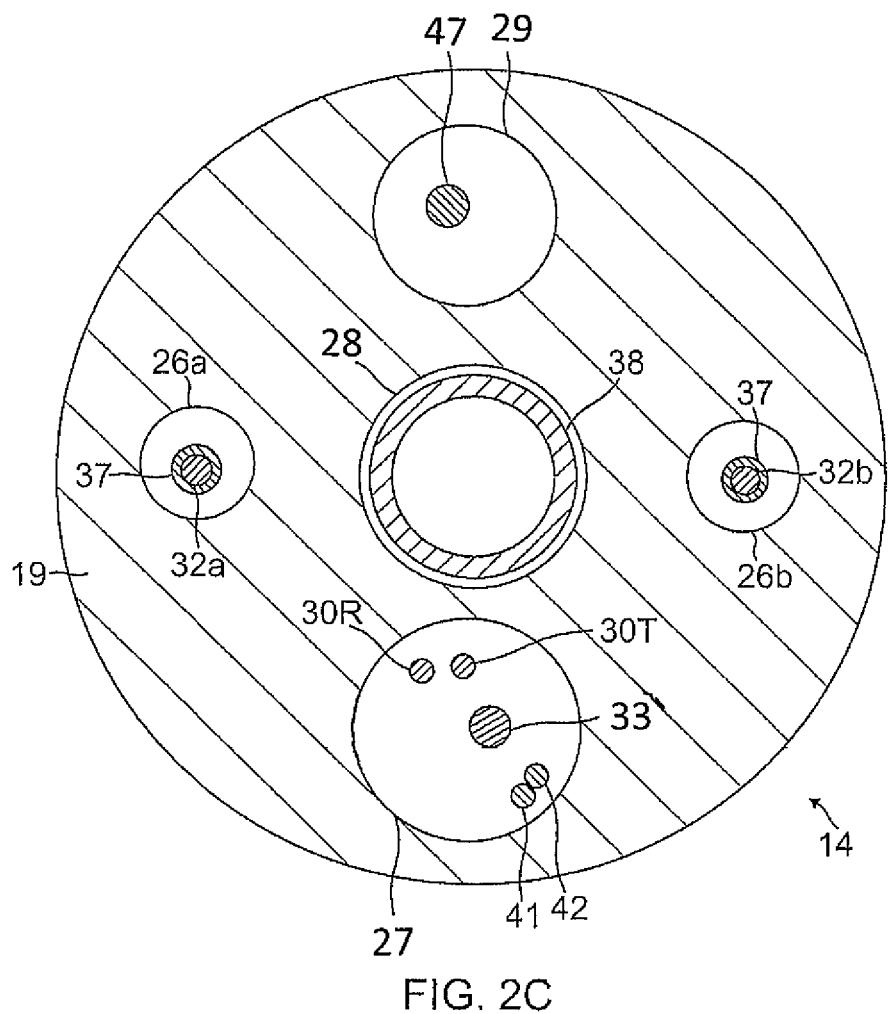
FIG. 2C is an end cross-sectional view of the intermediate section of FIG. 2B, taken along line C-C.

With reference to FIGS. 2A, 2B and 2C, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate puller members (e.g., puller wires), lead wires, and any other desired wires, cables or tubings. If desired, the inner surface of the outer wall 20 is lined with a stiffening tube 22 to provide improved torsional stability. A disclosed embodiment, the catheter has an outer wall 20 with an outer diameter of from about 0.090 inch to about 0.94 inch and an inner diameter of from about 0.061 inch to about 0.065 inch.

Distal ends of the stiffening tube 22 and the outer wall 20 are fixedly attached near the distal end of the catheter body 12 by forming a glue joint 23 with polyurethane glue or the like. A second glue joint (not shown) is formed between proximal ends of the stiffening tube 20 and outer wall 22 using a slower drying but stronger glue, e.g., polyurethane.

Components that extend between the control handle 16 and the deflectable section 14 pass through the central lumen 18 of the catheter body 12. These components include lead wires 30T and 30R for the tip electrode 17 and any ring electrodes 21 carried on the distal section 15, an irrigation tubing 38 for delivering fluid to the tip electrode, a cable 33 for a position location sensor 34 carried in the distal section 15, puller wires 32a, 32b for deflecting the intermediate section 14, and a pair of thermocouple wires 41, 42 to sense temperature at the distal section 15, and a safety tensile member or safety line 47 securing the tip electrode 17 to the catheter.

Illustrated in FIGS. 2A, 2B and 2C is an embodiment of the intermediate section 14 which comprises a short section of tubing 19. The tubing also has a braided mesh construction but with multiple lumens, for example lumens 26a, 26b, 27, 28, and 29. The first lumen 26a is off axis and carries a puller wire 32a for deflection of the intermediate section. For bi-directional deflection, the diametrically opposing off-axis second lumen 26b carries a second puller wire 32b. The third lumen 27 is also off-axis and carries the lead wires 30T and 30R, the thermocouple wires 41 and 42, and the sensor cable 33. The fourth lumen 28 is centered and on axis and carries the irrigation tubing 38. The fifth lumen 29, also off-axis, carries the safety line 47.

The tubing 19 of the intermediate section 14 is made of a suitable non-toxic material that is more flexible than the catheter body 12. A suitable material for the tubing 19 is braided polyurethane, i.e., polyurethane with an embedded mesh of braided stainless steel or the like. The size of each lumen is not critical, but is sufficient to house the respective components extending therethrough.

A means for attaching the catheter body 12 to the intermediate section 14 is illustrated in FIGS. 2A and 2B. The proximal end of the intermediate section 14 comprises an outer circumferential notch 25 that receives an inner surface of the outer wall 20 of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

Each puller wire 32a and 32b is preferably coated with Teflon®. The puller wires can be made of any suitable metal, such as stainless steel or Nitinol and the Teflon coating imparts lubricity to the puller wire. The puller wire preferably has a diameter ranging from about 0.006 to about 0.010 inch.

As shown in FIG. 2B, portion of each puller wire in the catheter body 12 passes through a compression coil 35 in surrounding relation to its puller wire. Each compression coil 35 extends from the proximal end of the catheter body 12 to at or near the proximal end of the intermediate section 14. The compression coils are made of any suitable metal, preferably stainless steel, and are tightly wound on themselves to provide flexibility, i.e., bending, but to resist compression. The inner diameter of the compression coil is preferably slightly larger than the diameter of the puller wire. Within the catheter body 12, the outer surface of the compression coil 35 is also covered by a flexible, non-conductive sheath 39, e.g., made of polyimide tubing. Each portion of the puller wires distal of the compression coil 35 may extend through a respective protective sheath 37 to prevent the puller wire from cutting into the tubing 19 of the intermediate section 14 during deflection.

Figure 3:
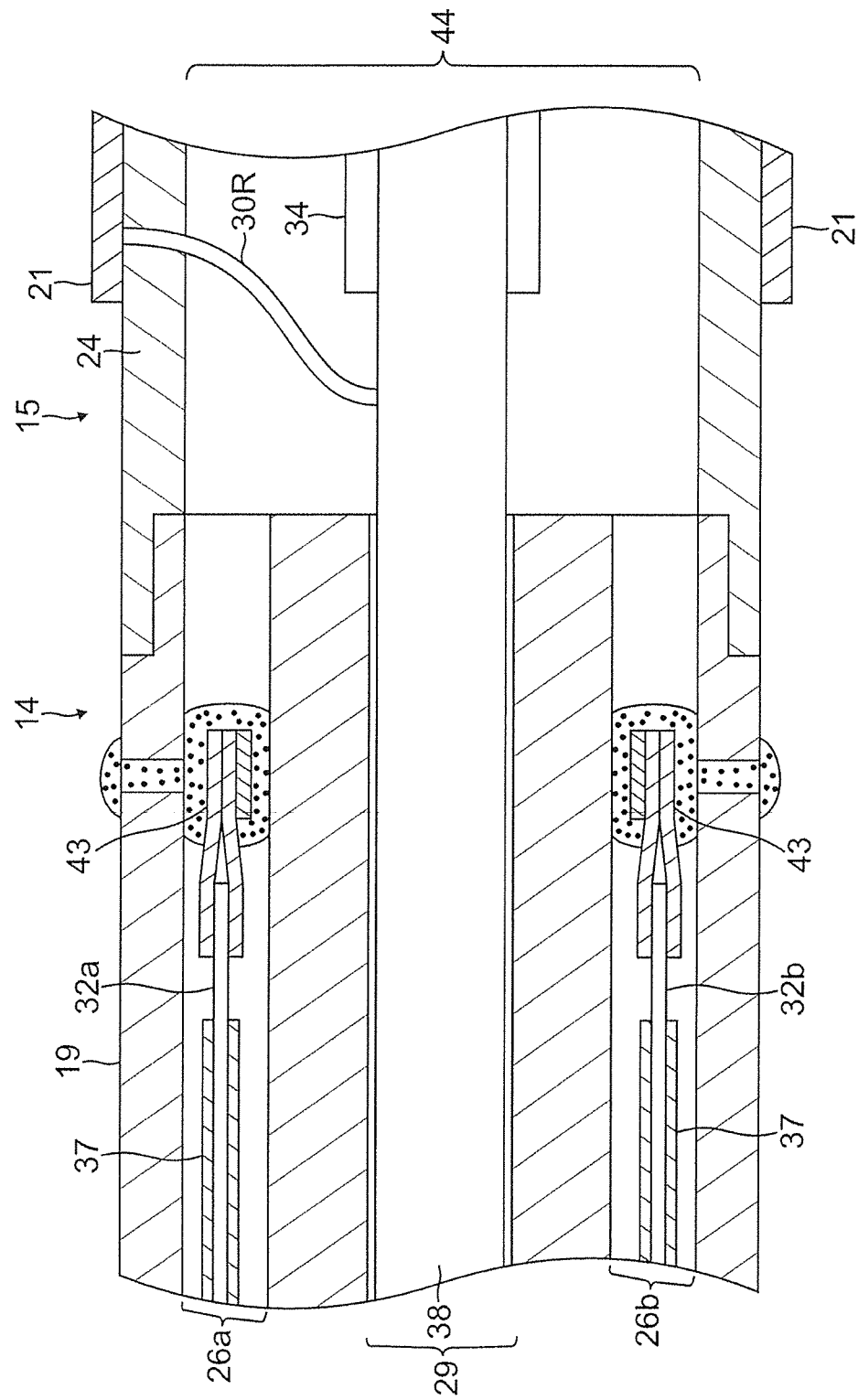
FIG. 3 is a side cross-sectional view of the catheter of FIG. 1, including a junction between the deflectable intermediate section and a distal section, taken along the second diameter.

Proximal ends of the puller wires 32 are anchored in the control handle 16. Distal ends of the puller wires 32 are anchored in the distal section 15, for example, by T-bars 43 as shown in FIG. 3. Separate and independent longitudinal movements of the puller wires relative to the catheter body 12, which results in, respectively, deflection of the intermediate section 14 along a plane, are accomplished by suitable manipulation of a deflection member of the control handle 16. [update] Suitable deflection members and/or deflection assemblies are described in co-pending U.S. Publication No. US2010/0168827 A1, published Jul. 1, 2010, entitled DEFLECTABLE SHEATH INTRODUCER, and U.S. Publication No. US2008/0255540 A1, published Oct. 16, 2008, entitled STEERING MECHANISM FOR BI-DIRECTIONAL CATHETER, the entire disclosures of both of which are hereby incorporated by reference.

Figure 4:
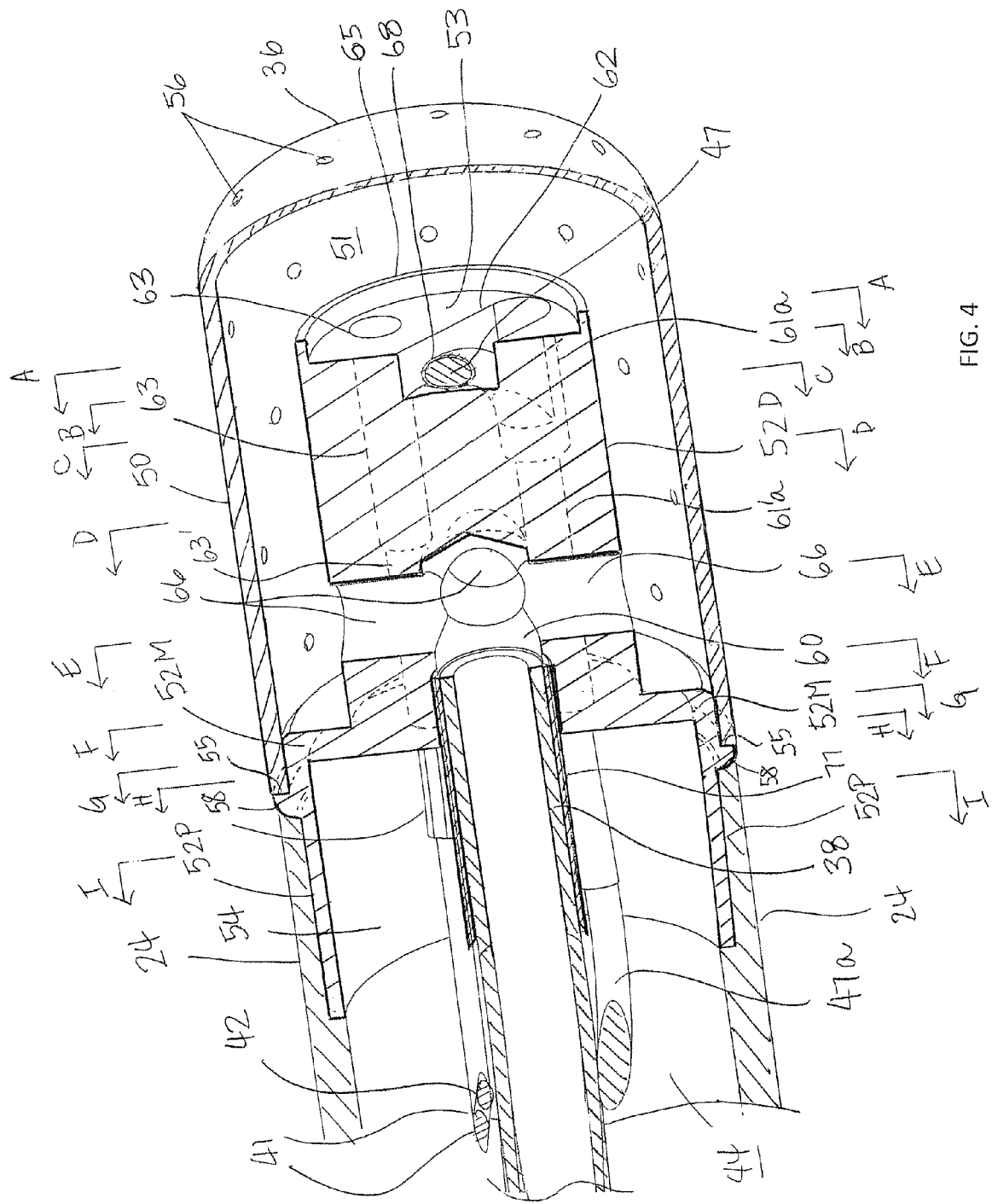
FIG. 4 is a perspective side cross-sectional view of a distal section of the catheter of FIG. 1, including a connector tubing and a tip electrode.
Figures 4A, 4B:
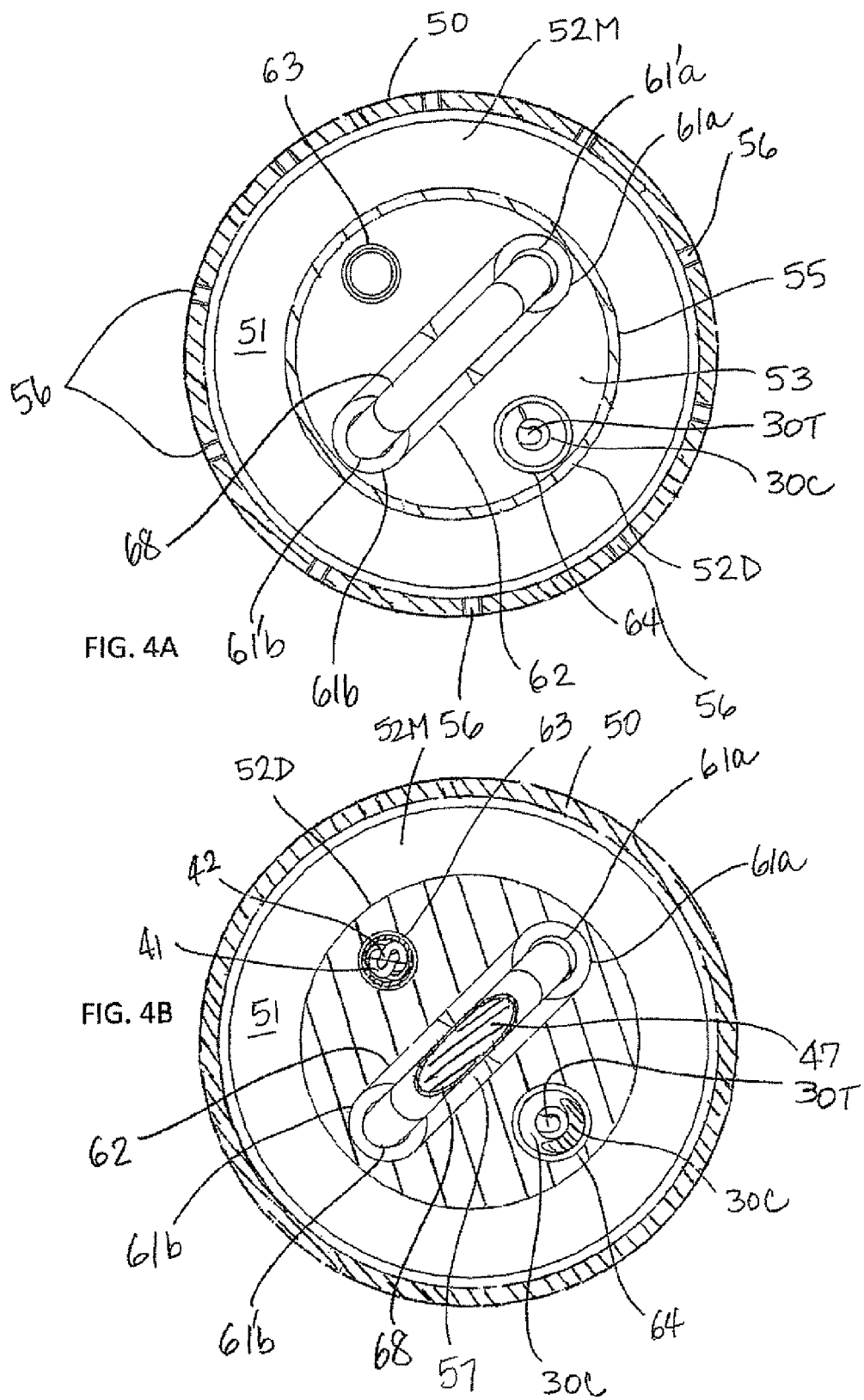
FIG. 4A is an end cross-sectional view of the tip electrode of FIG. 4, taken along line A-A.
FIG. 4B is an end cross-sectional view of the tip electrode of FIG. 4, taken along line B-B.
Figure 4C:
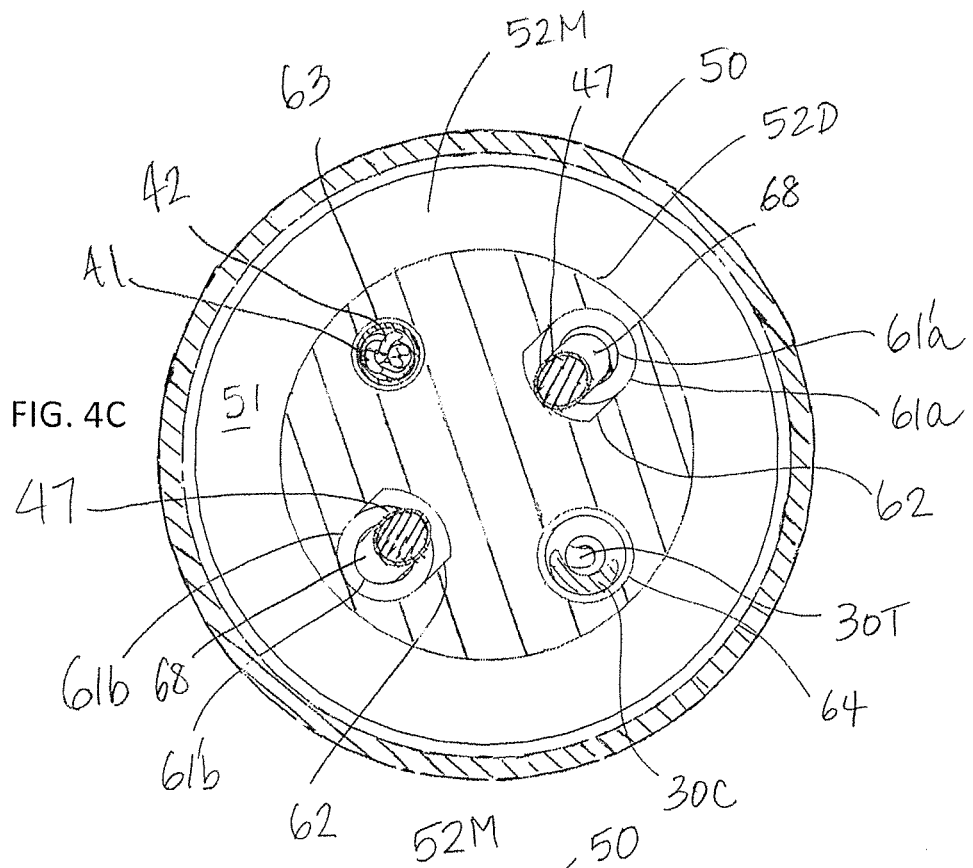
FIG. 4C is an end cross-sectional view of the tip electrode of FIG. 4, taken along line C-C.
Figure 4D:
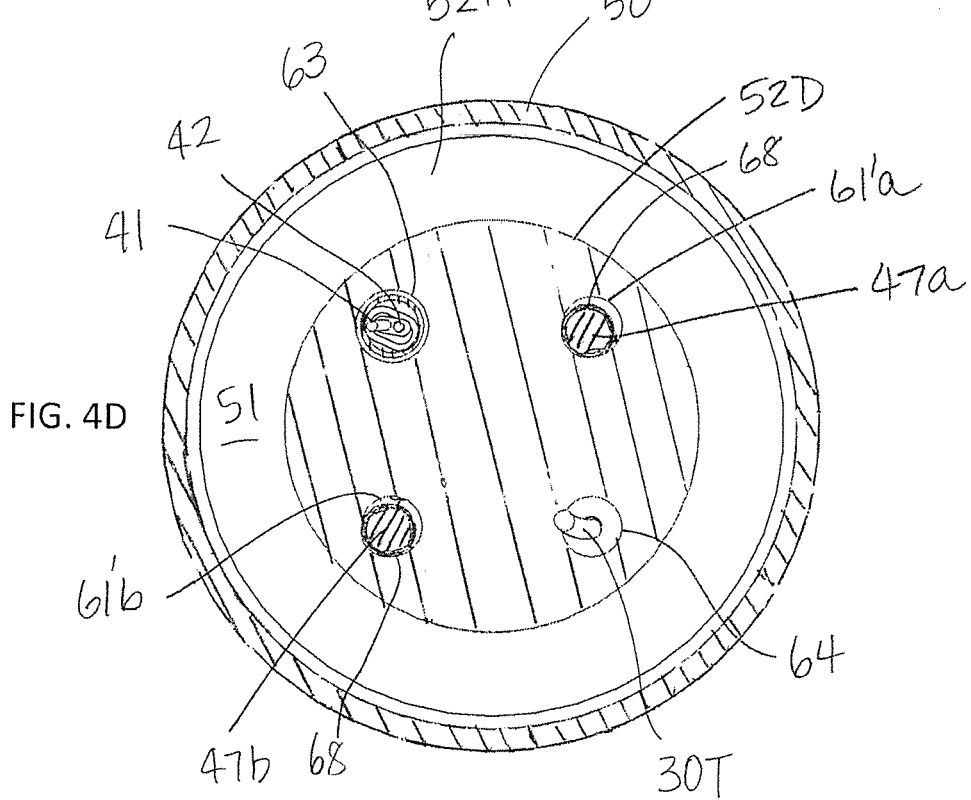
FIG. 4D is an end cross-sectional view of the tip electrode of FIG. 4, taken along line D-D.
Figure 4G:
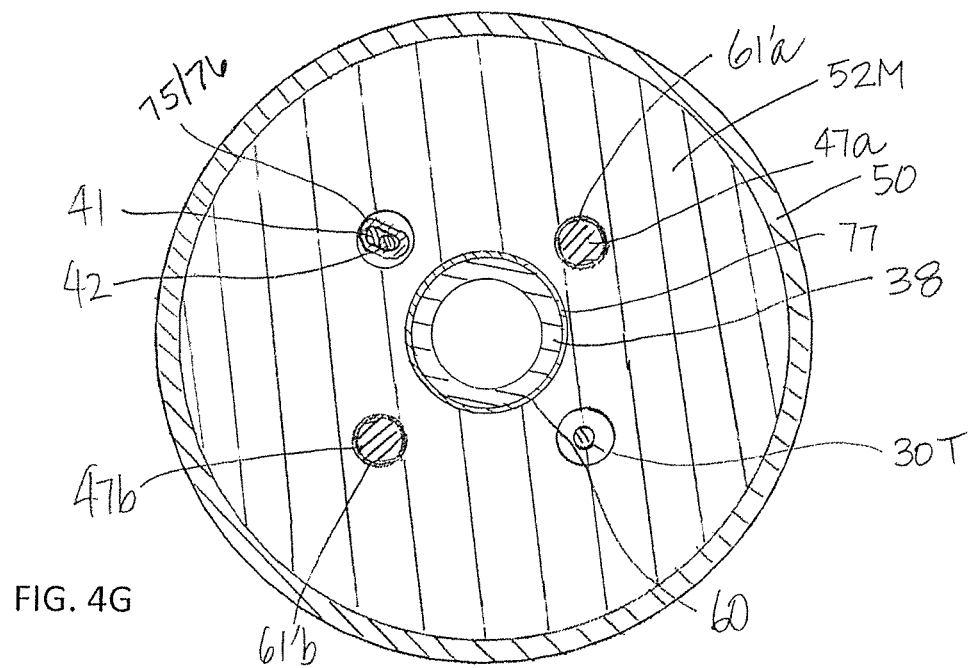
FIG. 4G is an end cross-sectional view of the tip electrode of FIG. 4, taken along line G-G.
Figure 4H:
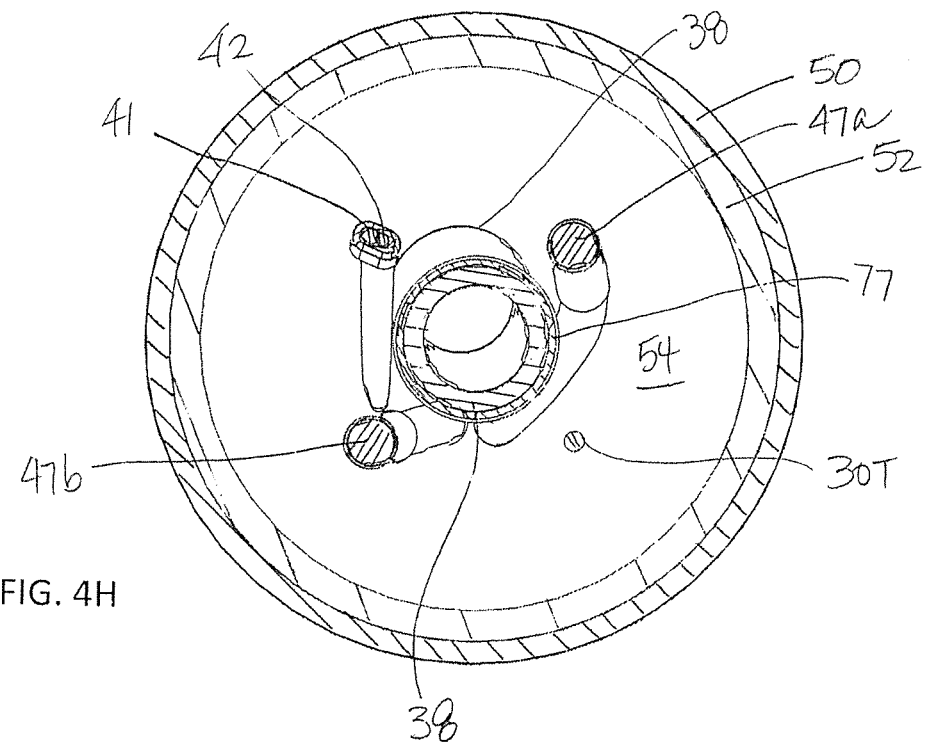
FIG. 4H is an end cross-sectional view of the tip electrode of FIG. 4, taken along line H-H.
Figure 41:
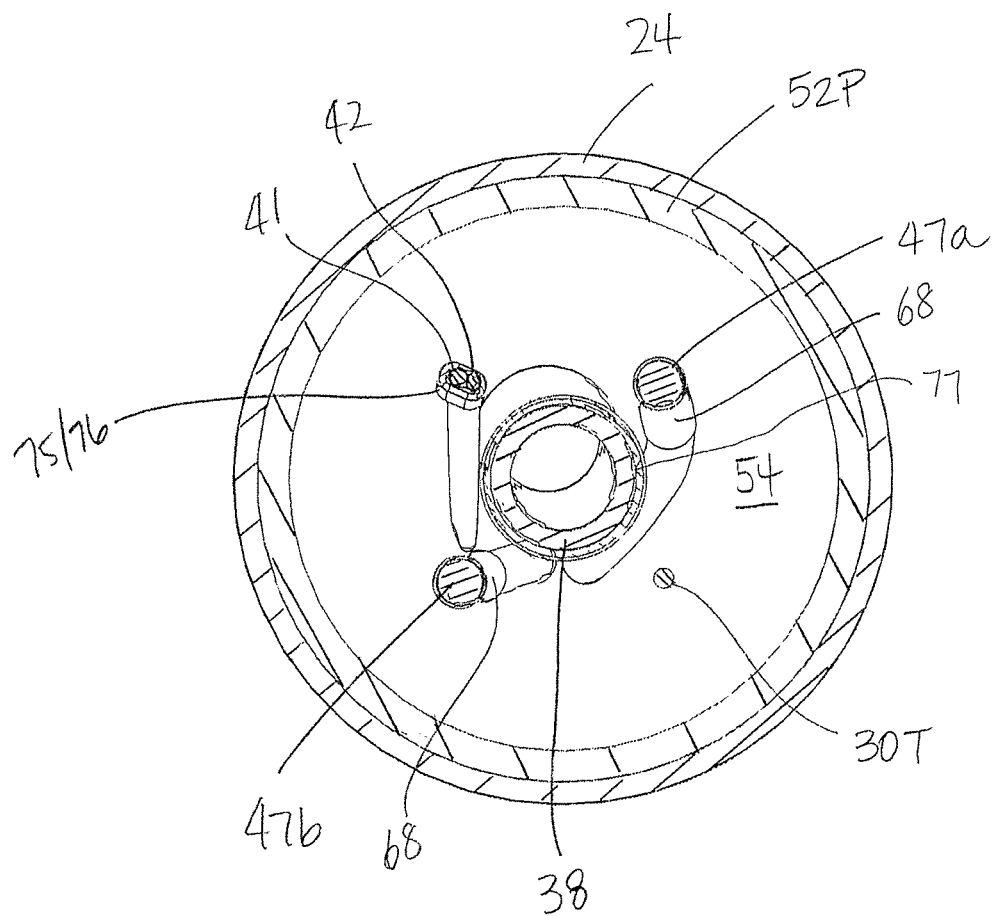
Figure 7:
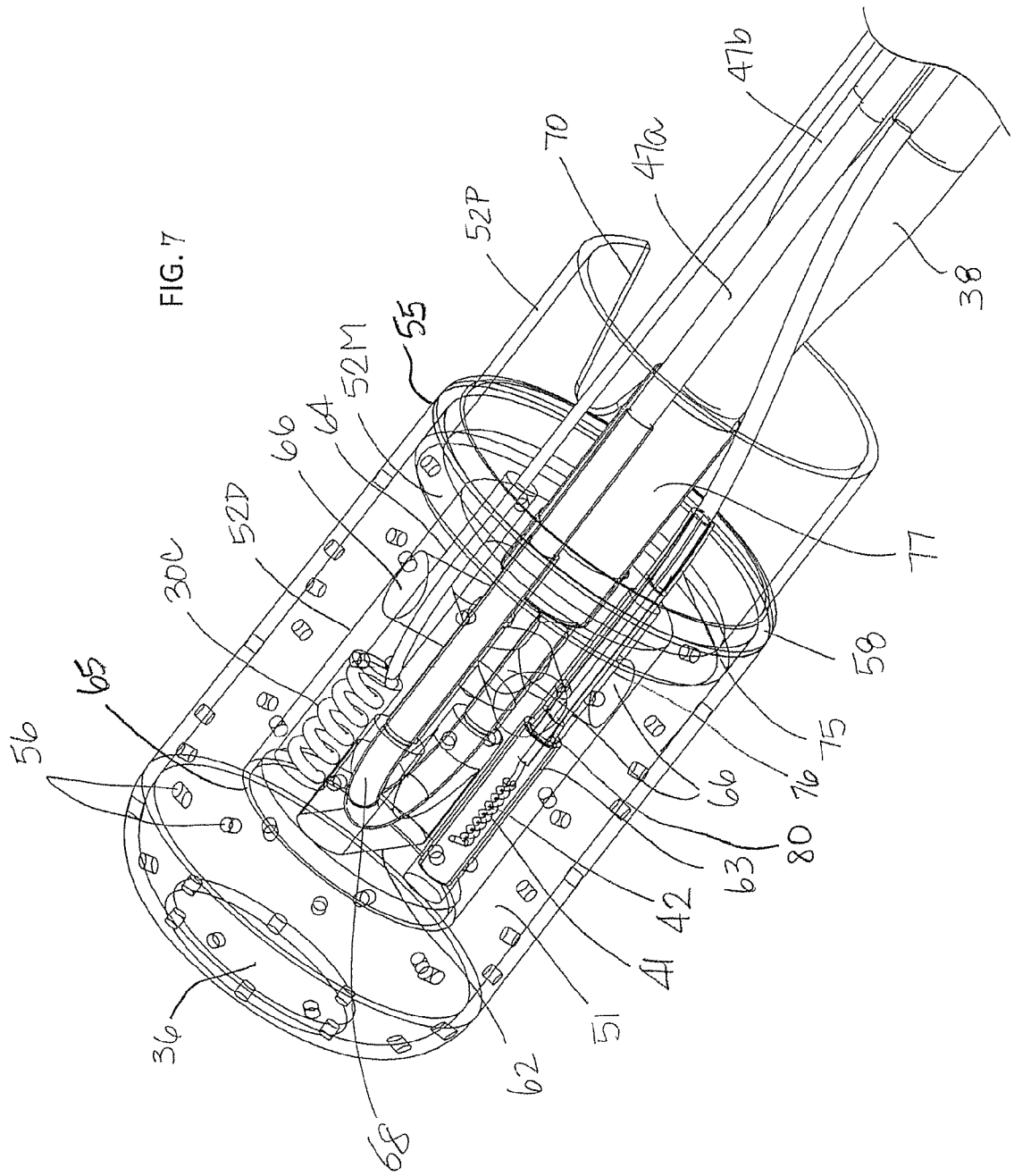
FIG. 7 is a perspective view of a perspective view of the distal section of FIG. 4, including a connector tubing and a tip electrode, with selected features shown in transparency.

With reference to FIGS. 4 and 7, at the distal end of the intermediate section 14 is the distal tip section 15 that includes the tip electrode 17 and a relatively short piece of non-conductive connector tubing or covering 24 between the tip electrode 17 and the intermediate section 14. In the illustrated embodiment, the connector tubing 24 has a single lumen 44 which houses the position sensor 34 (FIG. 3) and allows passage of components including the tip electrode lead wire 30T, the sensor cable 33, thermocouple wires 41 and 42, the safety line 47 and the irrigation tubing 38 into the tip electrode 17. The single lumen 44 of the connector tubing 24 allows these components to reorient themselves as needed from their respective lumens in the intermediate section 14 toward their location within the tip electrode 17. In the disclosed embodiment, the tubing 24 is a protective tubing, e.g., PEEK tubing, having a length ranging between 6 mm and 12 mm, more preferably about 11 mm.

Figure 5A:
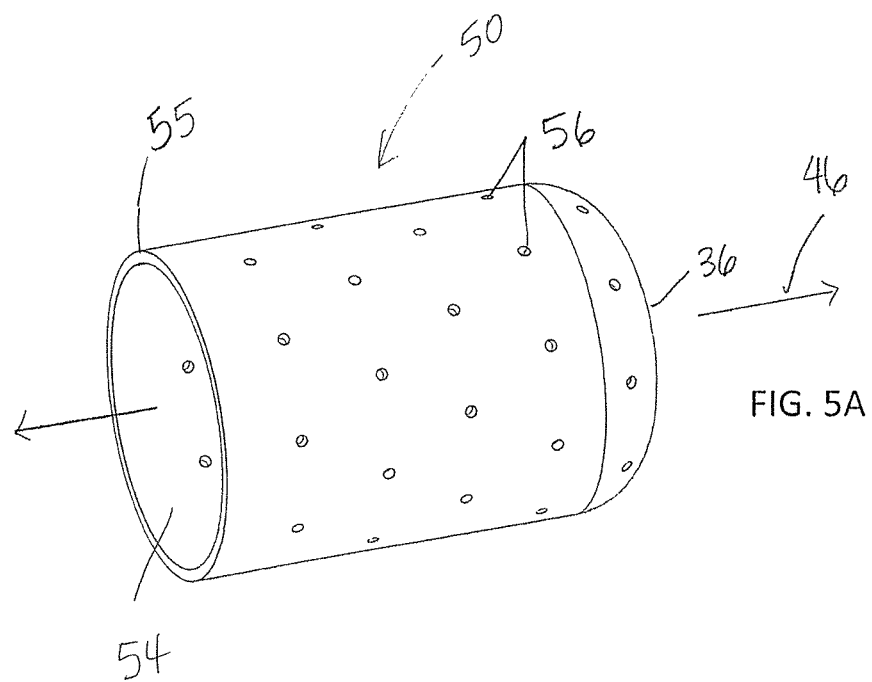
FIG. 5A is a perspective view of a tip electrode shell of FIG. 4.
Figure 5B:
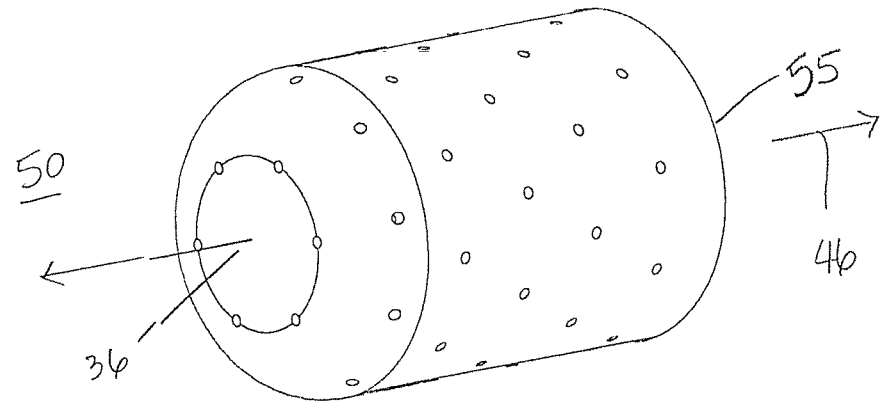
FIG. 5B is another perspective view of the tip electrode shell of FIG. 4.
Figure 6B:
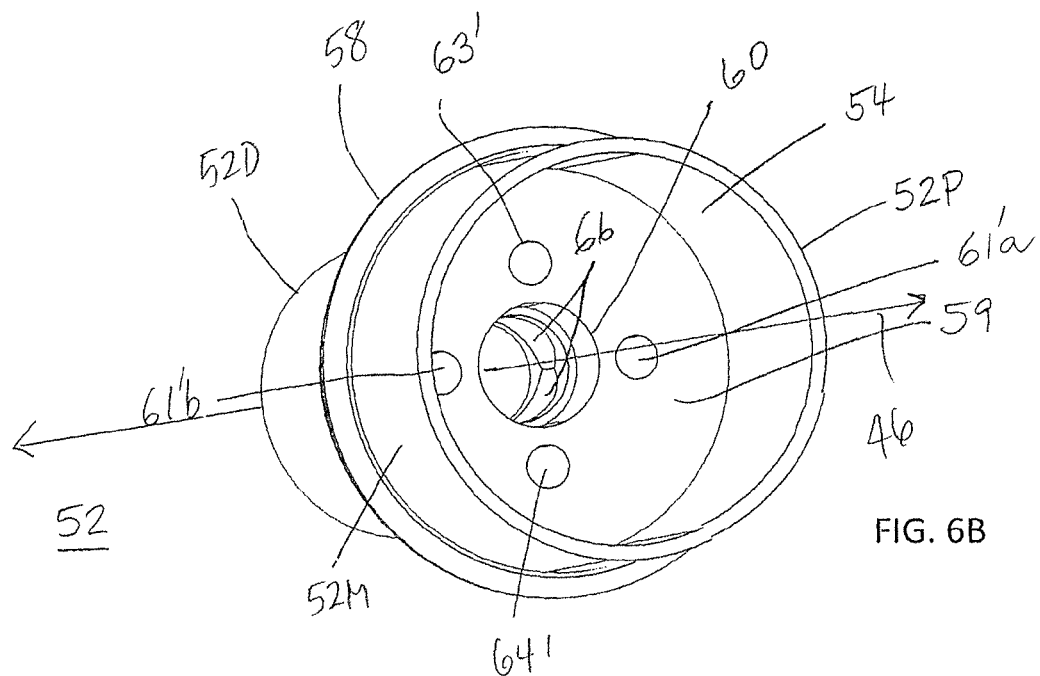
FIG. 6B is a another perspective view of the internal support member of FIG. 4.
Figure 6A:
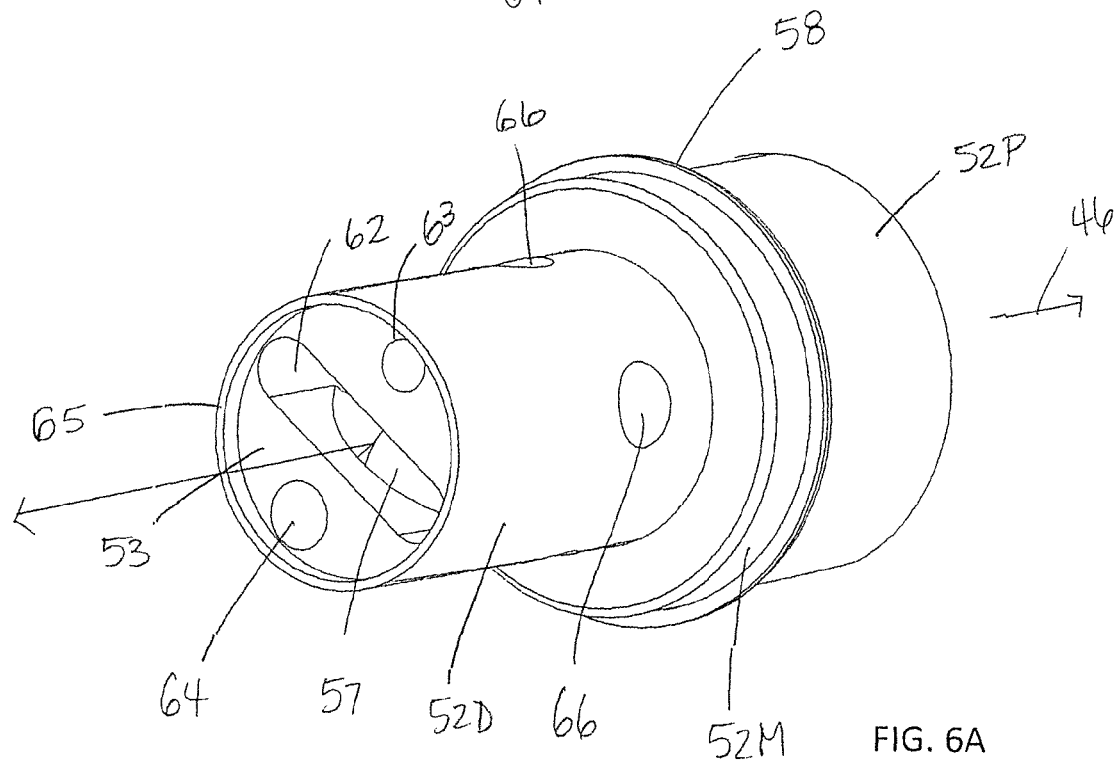
FIG. 6A is a perspective view of an internal support member of FIG. 4.

The tip electrode 17 defines a longitudinal axis 46 and is of at least a two-piece configuration that includes an electrically conductive dome shell 50 as shown in FIGS. 5A and 5B and an electrically conductive internal support member 52 as shown in FIGS. 6A and 6B, which jointly define a cavity or chamber 51 surrounded and enclosed by the shell 50 and the support member 52. The shell 50 is a hollow tubular or cylindrical shape and has a closed and rounded atraumatic distal end 36 and an open proximal end 54 defined by a rim 55 that is sealed by the support member 52 as described further below. Formed in the shell are a plurality of fluid ports 56 that allow fluid communication between the cavity 51 and outside the shell.

As show in FIGS. 4 and 7, the support member 52 forms a fluid-tight seal at the proximal end 54 of the shell 50. The support member 52 seals the interior cavity 51 of the shell 50, and the shell 50 and the support member 52 facilitate the provision of a plenum condition within the cavity; that is, where fluid is forced or delivered into it for a more uniform distribution through fluid ports 56 formed in the shell.

With reference to FIGS. 4A-4I, the support member 52 along its length has circular cross-section of varying sizes. The member 52 includes a plug mid-portion 52M, a narrower rod-like distal portion 52D (with a smaller radius) and a wider proximal hollow cylindrical portion 52P or "skirt" (with a larger radius). Each of the plug portion 52M and the rod-like distal portion 52D is generally of a solid form. A distal surface 53 of the rod portion 52D is recessed such that an annular ring 65 surrounds the surface 53. The plug portion 52M sits with a snug fit in the open proximal end 54 of the shell 50 surrounded by the rim 55 so as to plug the end 54. The rod-like distal portion 52D extends into the cavity 51 inside the shell. A raised annular flange 58 provided on an outer surface of the plug portion 52 abuts with the proximal end 54 of the shell 50 to limit the extent to which the plug portion 52M and the rod portion 52D can extend into the cavity 51 inside the shell 50. The shell is attached to the support member 52 along the annular flange 58. The hollow cylindrical portion 52P is received in a distal end of the tubing 24 of the distal section 15. The portion 52P receives components extending from the tubing 24 and into the tip electrode 17.

To accommodate the components passing into the tip electrode, the plug portion 52M and the rod portion 52D have a plurality of axial passages extending therethrough, including a center fluid passage 60, two off-axis diametrically-opposing passages 61A and 61B, third and fourth off-axis passages 63 and 64. Each of the passages 61A, 61B, 63 and 64 occupies a quadrant in the circular cross-sectional space of the plug and rod portions 52M and 52D. In the illustrated embodiment of FIG. 4E, the passages 61A and 61B occupy one pair of opposing quadrants (e.g., Quadrants I and III) and passages 63 and 64 occupy another pair of opposing quadrants (e.g., Quadrants II and IV). As such, there is efficient use of the space within the tip electrode 17 with minimal interference between components extending through each passage.

The center fluid passage 60 is formed as a blind hole that extends from a proximal surface 59 of the plug portion 52M and distally into the rod portion 52D by a predetermined distance D. In the illustrated embodiment, the distance is about ⅓ of a length L of the rod portion 52. At a distal end of the blind hole transverse fluid passages 66 are arranged radially about the blind hole. The passage 66 receives a distal end of the irrigation tubing 38 for passing fluid delivered by the irrigation tubing 38 to the tip electrode 17 for perfusion inside the cavity 51 and to outside the tip electrode 17 via the fluid ports 56. Distal portion of the irrigation tubing 38 may be surrounded by a protective tubing 77, for example, polyimide tubing.

The third passage 63 extends between the proximal surface 59 of the plug portion 52M and the distal surface 53 of the rod portion 52D. From the tubing 24, the thermocouple wires 41 and 42 extend through the third passage 63 with their distal ends anchored near the distal surface 53 of the rod portion 52D. Distal ends of the thermocouple wires 41 and 42 may be covered in a nonconductive cover or sheath 75, for example, a polyester heat shrink sleeve. The sheath 75 is an electrically insulating, second protective covering over the thermocouple wires (proximal to thermocouple junction 80, FIG. 7) to prevent abrasion against the support member 52. Surrounding a distal portion of the sheath 75 may be another nonconductive tubing 76 (FIG. 7), for example, a polyimide tubing. The tubing 76 is constructed of a thermally conductive material which provides electrical isolation between the thermocouple junction 80 and the support member 52 which is energized with RF potential.

The fourth passage 64 also extends between the proximal surface 59 of the plug portion 52M and the distal surface 53 of the rod portion 52D. From the tubing 24, the lead wire 30T for the tip electrode 17 extends through the passage 64 with its distal end anchored near the distal surface 53 of the rod portion 52D.

For a wrap-around safety line configuration, the passages 61A and 61B are connected and in communication with each other at their distal ends via a curved transverse passage 62 forming a rounded distal surface defining an outwardly radiused distal end 57. Accordingly, the passages 61A, 61B and 62 form a U-shaped passage in the support member 52 that passes through the plug portion 52M and the rod portion 52D where it defines and forms an outwardly convex distal end 57. In the illustrated embodiment, the passages 61A and 61B extend sufficiently distally such that the transverse passage 62 and the distal end 57 are exposed and accessible at the distal end of the rod portion 52D. The U-shaped passage generally encircles or wraps around the distal end 57. Thus, with the safety line 47 passing through the U-shaped passage and around the distal end 57, the safety line 47 reliably secures the support member 52, and the shell 50 affixed thereon, to the catheter. That is, the support member 52 is directly secured by the safety line. There is no intermediate structure or parts between the safety line and the member 52, and there are no knots or tight bends in the safety line that can induce stress concentrations. To protect the safety line, a friction-reducing protective sleeve 68 covers the section of the safety line extending over the curved transverse passage 62. The sleeve 68 may be of any suitable nonconducting material, for example, polyimide.

The radiused distal end 57 circumscribed by the transverse passage 62 of the U-shaped passage has a uniform curvature defined by a predetermined diameter so that the safety line can be redirected by 180 degrees ("double back" on itself) to form a secure attachment to the tip electrode with minimal stress concentrations. In accordance with a feature of the present invention, a ratio of no less than about 3:1 of the diameter of the uniform curvature to a diameter of the safety line minimizes, if not avoids, inducement of stress concentration on the safety line. For example, where the safety line 47 has a diameter of about 0.004 inch, the diameter defining the curvature of the transverse passage 62 should be at least about 0.012 inch.

The present invention is also directed to a method of assembly of the tip electrode 17, which includes feeding or installing various components into the tip electrode 17 from its distal end. The method includes providing the support member 52, without the shell 50 mounted, with at least a distal portion of the U-shaped passage or the radiused distal end 57 exposed and accessible to an assembly person. As such, the passages 61A/61B, 62, 63 and 64 can be accessed from the distal end of the support member 52, and component(s), including, for example, the lead wire 30T, the thermocouple wires 41 and 42 and/or the safety line 47 can be fed into the support member 52 from its distal end. For example, each end of the safety line 47 is fed into a respective one of passages 61A and 61B, whereupon a mid-section of the safety line straddles the radiused distal end. Moreover, proximal ends of the thermocouple wires 41 and 42 are fed proximally into the passage 63 from the distal surface 53. Likewise, a proximal end of the lead wire 30 is fed proximally into the passage 64 from the distal surface 53. With respect to passages 63 and 64, their respective distal ends 63D and 64D may have openings with a greater width or diameter to accommodate enlarged distal ends of the lead wire 30T and/or thermocouple wires 41 and 42 for purposes of anchoring the distal ends in the support member 52. In the illustrated embodiment, a distal end of the lead wire 30T has an enlarged coil 30D and distal ends of the thermocouple wires have an enlarged crimped foldback 41/42D. Advantageously, the passage distal ends 63D and 64D are sufficiently large to receive the coil 30D and the crimped foldback 41/42D, whereas the proximal remainder of the passages 63 and 64 are sufficiently narrow to abut and anchor the coil and the crimped foldback. It is noted that the enlarged ends 63D and 64D of the passages 63 and 64 are longitudinally offset relative to the transverse fluid passages 66 so that the ends 63D and 64D and the fluid passages 66 need not compete with each other for space in the circular cross-sectional area of the support member 52. In the illustrated embodiment, the enlarged ends 63D and 64D are distal of the transverse fluid passages 66.

When the components, including the lead wire, thermocouple wires and safety line have been installed in the internal support member 52, the recessed distal surface 53 of the rod portion 52D may be filled or packed with a suitable adhesive so as to seal the distal end of the rod portion against fluid leakage from the cavity 51 into the passages 61A/61B, 62, 63 and 64. The shell 50 is then mounted on the rod portion 52D with the rod portion 52D extending into the cavity 51 with the rim 55 abutting the raised annular flange 58. The rim and the flange are soldered to fixedly attach the shell to the support member 50.

In one embodiment, the safety line 47 is made of a high modulus fiber material, preferably having a tensile modulus substantially in the range of 5,000 ksi (35,000 MPa) to about 20,000 ksi (140,000 MPa), more preferably about 9,750 ksi (68,000 MPa), such as High Molecular Density Polyethylene (e.g., Spectra™ or Dyneema™), a spun para-aramid fiber polymer (e.g., Kevlar™) or a melt spun liquid crystal polymer fiber rope (e.g., Vectran™), or a high strength ceramic fiber (e.g., Nextel™). These materials tend to be flexible, providing suitable durability. Further, they are substantially non-stretching and nonmagnetic so that they generally appear transparent to an MRI. The low density of the material causes it to be generally transparent to an x-ray machine. The materials can also be nonconductive to avoid shorting. Vectran™, for example, has high strength, high abrasion resistance, is an electrical insulator, nonmagnetic, is polymeric, and has low elongation under a load.

Preferably, the safety line 47 has a tensile strength ranging between about 300 ksi (2,000 MPa) to 1,500 ksi (10,400 MPa), more preferably around 450 ksi (3,100 MPa). This would allow the safety line to have a higher strength than conventional steel wires as well as a reduced cross-section. In one embodiment, the high modulus fiber material is braided.

The shell 50 and the internal support member 52 are constructed of a biocompatible metal, including a biocompatible metal alloy. A suitable biocompatible metal alloy includes an alloy selected from stainless steel alloys, noble metal alloys and/or combinations thereof. In one embodiment, the shell is constructed of an alloy comprising about 80% palladium and about 20% platinum by weight. In an alternate embodiment, the shell 50 and the member 52 are constructed of an alloy comprising about 90% platinum and about 10% iridium by weight. The shell can formed by deep-drawing manufacturing process which produces a sufficiently thin but sturdy shell wall that is suitable for handling, transport through the patient's body, and tissue contact during mapping and ablation procedures.

Ring electrodes 21 (FIGS. 1 and 3) may be mounted on the connector tubing 24 of the distal section 15. They may be made of any suitable solid conductive material, such as platinum or gold, preferably a combination of platinum and iridium. The ring electrodes can be mounted onto the connector tubing 24 with glue or the like. Alternatively, the ring electrodes can be formed by coating the tubing 24 with an electrically conducting material, like platinum, gold and/or iridium. The coating can be applied using sputtering, ion beam deposition or an equivalent technique. The number of the ring electrodes on the tubing 24 can vary as desired. The rings may be monopolar or bi-polar. In the illustrated embodiment, there is a distal monopolar ring electrode and a proximal pair of bipolar ring electrodes. Each ring electrode is connected to a respective lead wire 30R. A ring electrode 21 may be mounted immediately proximal of the exposed portion of the tip electrode 17. As such, a notch 70 (FIG. 7) may be formed in the skirt 52P of the support member 52 to allow lead wire 30R to be connected to the ring electrode.

As understood by one of ordinary skill in the art, each lead wire 30R is attached to its corresponding ring electrode by any suitable method. A preferred method for attaching a lead wire to a ring electrode involves first making a small hole through the wall of the tubing 24 (FIG. 3). Such a hole can be created, for example, by inserting a needle through the non-conductive covering and heating the needle sufficiently to form a permanent hole. The lead wire is then drawn through the hole by using a microhook or the like. The end of the lead wire is then stripped of any coating and welded to the underside of the ring electrode, which is then slid into position over the hole and fixed in place with polyurethane glue or the like. Alternatively, each ring electrode is formed by wrapping a lead wire 30R around the non-conductive tubing 24 a number of times and stripping the lead wire of its own insulated coating on its outwardly facing surfaces.

The tip electrode 17 is electrically connected to a source of ablation energy (not shown) by the lead wire 30T. The ring electrodes 21 are electrically connected to an appropriate mapping or monitoring system by respective lead wires 30R.

The lead wires 30T and 30R pass through the lumen 27 (FIG. 2A) of the tubing 19 of the deflectable intermediate section 14 and the central lumen 18 of the catheter body 12. The portion of the lead wires extending through the central lumen 18 of the catheter body 12, and proximal end of the lumen 27 can be enclosed within a protective sheath (not shown), which can be made of any suitable material, preferably polyimide. The protective sheath is anchored at its distal end to the proximal end of the intermediate section 14 by gluing it in the lumen 27 with polyurethane glue or the like. Each electrode lead wire has its proximal end terminating in a connector at the proximal end of the control handle 16.

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention. It is understood that the drawings are not necessarily to scale. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A catheter, comprising:
   an elongated catheter body;
   a tip electrode distal to the catheter body, the tip electrode comprising:
      a support member having a passage portion defining a rounded distal surface; and
      an electrically conductive shell mounted on the support member; and
   a safety tensile member having a tensile portion positioned in the passage portion to pass around the rounded distal surface.

2. The catheter of claim 1, wherein the safety tensile member has two ends, at least one of which is anchored to the catheter body.

3. The catheter of claim 2 further comprising a control handle, wherein the at least one end of the safety tensile member is anchored in the catheter handle.

4. The catheter of claim 1, wherein the passage portion is U-shaped.

5. The catheter of claim 1, wherein the safety tensile member has two proximal portions extending in parallel through the catheter body.

6. The catheter of claim 1, wherein the shell and the support member define a cavity therebetween and the support member has at least one additional passage providing fluid communication between the catheter body and the cavity.

7. The catheter of claim 6, wherein the shell has at least one fluid port configured to allow fluid communication between the cavity and outside the shell.

8. The catheter of claim 1, wherein the support member has at least one additional passage configured to receive at least one component passing between the catheter body and the tip electrode.

9. The catheter of claim 8, wherein the at least one component has an enlarged distal end and the at least one additional passage has a wider distal portion to receive and anchor the enlarged distal end.

10. A catheter, comprising:
    a tubing having a proximal end and a distal end;
    a tip electrode distal to the tubing, the tip electrode comprising:
       an electrically conductive shell having a cavity, a dome distal end and an opening at its proximal end; and
       a support member having a plug portion situated in the opening, a hollow proximal portion received in the distal end of the tubing, and a distal portion extending into the cavity of the shell, the support member having a U-shaped passage portion defining a rounded distal surface; and
    a safety tensile member having a tensile portion extending through the U-shaped passage portion to pass around the rounded distal surface.

11. The catheter of claim 10, wherein the support member has at least one additional passage providing fluid communication between the tubing and the cavity.

12. The catheter of claim 10, wherein the shell has at least one fluid port configured to allow fluid communication between the cavity and outside the shell.

13. The catheter of claim 10, wherein the support member has at least one additional passage configured to receive at least one component passing between the tubing and the tip electrode.

14. The catheter of claim 13, wherein the at least one component has an enlarged distal end and the at least one additional passage has a wider distal portion to receive and anchor the enlarged distal end.

15. A method of manufacturing a catheter tip electrode comprising:
   providing a tip electrode comprising a support member and an electrically conductive shell;
   forming in the support member a passage defining a rounded distal surface;
   extending a safety tensile member in the passage to pass around the rounded distal surface, the safety tensile member having two portions extending proximally of the rounded distal surface; and
   mounting the shell on the support member.

16. The method of manufacturing of claim 15, wherein the rounded distal surface is exposed.

17. The method of claim 16, further comprising sealing the rounded distal surface prior to mounting the shell on the support member.

18. The method of claim 15, further comprising forming in the support member at least one additional passage.

19. The method of claim 18, further comprising providing an irrigation tubing in the at least one additional passage.

20. The method of claim 18, further comprising providing in the at least one additional passage a component selected from a group consisting of a lead wire and a thermocouple wire pair.

21. The method of claim 20, further comprising:
   providing an enlarged distal portion in the at least one additional passage; and
   providing an enlarged distal end in the component for anchoring in the enlarged distal portion of the at least one additional passage.

* * * * *